United States Patent [19]

Fleury

[11] 3,932,404
[45] Jan. 13, 1976

[54] PROCESS FOR MAKING PYRAZINES FROM 2-AZA-1,3-BUTADIENES

[75] Inventor: Jean-Pierre Louis Fleury, Mulhouse, France

[73] Assignee: Pechiney Ugine Kuhlmann, Paris, France

[22] Filed: Mar. 21, 1973

[21] Appl. No.: 343,590

[30] Foreign Application Priority Data
Jan. 20, 1972 France .............................. 72.01854

[52] U.S. Cl. ..................... 260/250 BC; 260/247.2 B; 260/250 BN; 260/251.5; 260/293.65; 260/293.87; 260/326.43; 260/465 D
[51] Int. Cl.² ..................................... C07D 241/28
[58] Field of Search ...... 260/250 R, 250 B, 250 BN, 260/250 Q, 250 BC

[56] References Cited
FOREIGN PATENTS OR APPLICATIONS
320,494  2/1972  U.S.S.R. .......................... 260/250 B OTHER PUBLICATIONS
Smith, "The Chemistry of Open–Chain Organic Nitrogen Compounds," Vol., I, W. A. Benjamin, Inc., N.Y., 1965, p. 214.

*Primary Examiner*—R. Gallagher
*Attorney, Agent, or Firm*—Browne, Beveridge, DeGrandi & Kline

[57] ABSTRACT

Process for the preparation of an amino-pyrazine falling within the formula:

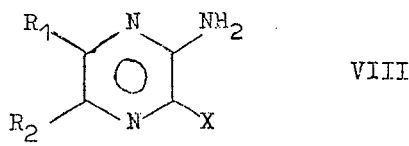

VIII in which $R_1$ and $R_2$ each represent a hydrogen atom, or an alkyl or aryl group, or together with the carbon atoms of the pyrazine ring form a cyclic hydrocarbon having 5 to 7 carbon atoms, and X represents a cyano, carboxy, carbonamido, alkoxy-carbonyl or aryloxycarbonyl group which comprises subjecting a 2-aza-1,3-butadiene of the general formula:

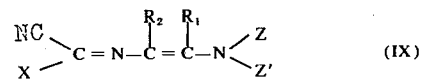

(IX)

wherein Z and Zi each represent an alkyl group or together with the nitrogen atom form a heterocyclic compound possibly containing another hetero atom to the action of ammonia and reacting the 4-amino-2-aza-1,3-butadiene of formula

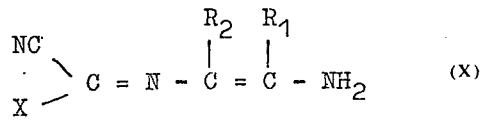

(X)

thus obtained with a basic agent: novel compounds of formula VIII in which $R_1$ and $R_2$ each represent a different alkyl or aryl group or together with the carbon atoms of the pyrazine ring form a cyclic hydrocarbon containing 5 to 7 carbon atoms: intermediate compounds of formula:

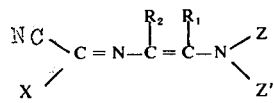

wherein X, $R_1$ and $R_2$ have the meanings given above and Z and Z' each represent an alkyl group or together with the nitrogen atom form a heterocyclic compound possibly containing another hetero-atom; and intermediate compounds of the formula:

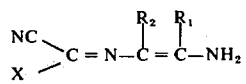

wherein X, $R_1$ and $R_2$ have the meanings given above.

15 Claims, No Drawings

PROCESS FOR MAKING PYRAZINES FROM 2-AZA-1,3-BUTADIENES

The present invention relates to a new process for the preparation of aminopyrazines, new aminopyrazines and new intermediate products obtained by this process. The aminopyrazines may themselves be used as intermediate products for the preparation of medicaments (Dutch Applications No. 6,409,712, 6,409,713, 6,409,714, 6,409,715, 6,409,716 and 6,409,717 of Oct. 1, 1965 and 6,501,301 of Oct. 4, 1965.

Several methods have been proposed for the synthesis of aminopyrazines. Thus, aminopyrazines may be obtained by condensing the aminomalonic derivative of formula II with the dicarbonyl derivative of formula I (see the Dutch Applications mentioned above, Belgian Patent No. 639,389 or O. Vogl and E. C. Taylor, J. Amer.Chem.Soc., 1959, 81, 2472).

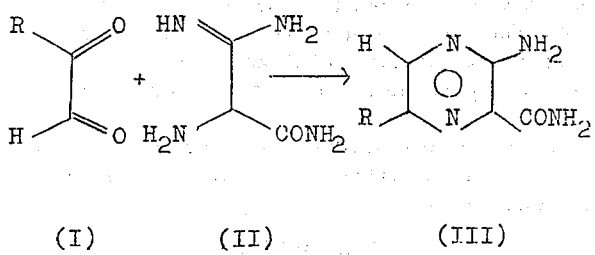

(I)     (II)     (III)

The carboxamide of formula III may be converted into the corresponding acid and ester. The following comments may be made about this process:

The starting products are not very easy to obtain. Thus, the malonic derivative of formula II must be prepared from ethyl cyanoacetate in 4 very complex stages. On the other hand, the yield of the condensation is moderate. Finally, this method only leads to pyrazines which are not substituted in the 5-position.

Another method consists in reacting the pyrimidine of the formula IV (which itself is derived from the amide of formula II mentioned above) with a dicarbonyl derivative of formula (V)

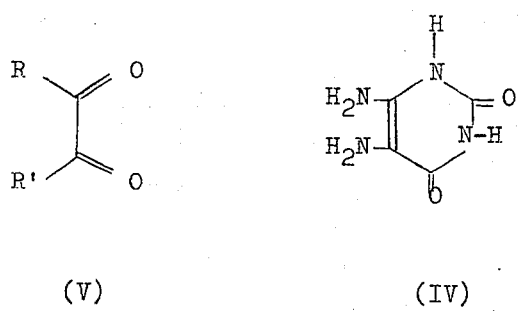

(V)     (IV)

If R and R' are two different groups, two isomeric pteridines of formulae (VI) and (VI') are thus obtained; the latter may be hydrolysed to pyrazines of formula (VII) and (VII');

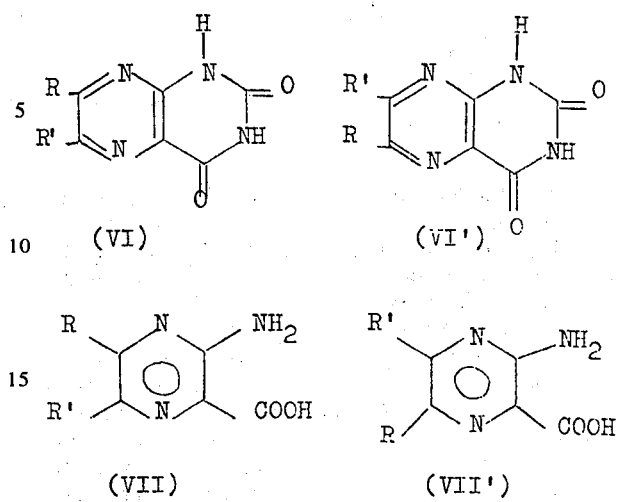

(VI)     (VI')

(VII)     (VII')

but the separation of the two isomers is difficult and the assigning of a structure is problematical, if not impossible. For this reason, this method of preparation (see above patent and J. Weijlard, M. Tischler, A. E. Erikson, J.Amer. Chem.Soc., 1945 67, 802 and E. C. Taylor, J.Amer.Chem. Soc., 1952, 74, 1651) has generally only been used for pyrazines having identical R and R' groups.

Moreover, the 3-amino-2-cyano-pyrazines are not directly available and are obtained by dehydration of the corresponding amines (J. H. Jones, E. J. Cragoe Jr., J. Medicin. Chem., 1958, 11, 322, A. Albert, K. Ohta, Chem. Communic., 1969, 1168).

It has now been found that pyrazines of the following general formula:

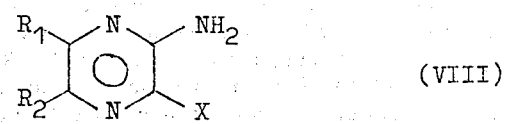

(VIII)

in which $R_1$ and $R_2$ represent hydrogen atoms or alkyl or aryl groups, or form with the carbon atoms of the pyrazine ring a cyclic hydrocarbon containing 5 to 7 carbon atoms, and X represents a cyano, carboxy, carbonamido, alkoxycarbonyl or aryloxy-carbonyl group may be obtained by a new method, which is not limited like some of the processes described above. The process according to the invention is specific and leads to single pyrazines of well defined structure, and it uses readily available starting substances.

According to the present invention a process for the preparation of pyrazines of general formula VIII is provided which comprises subjecting a 2-aza-1,3-butadiene of general formula (IX) to transamination by the action of ammonia to produce an azadiene of general formula (X) and then reacting this with a basic agent to produce a pyrazine of formula (VIII).

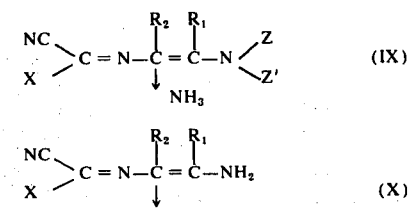

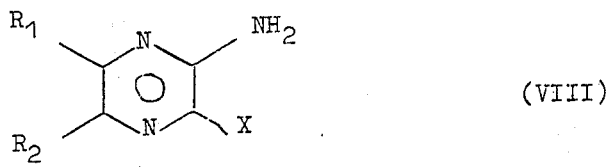

Neither the butadines of general formula IX nor those of general formula X are described in the literature. Those compounds of formula (VIII) in which $R_1$ and $R_2$ represent identical groups are known but the others are novel.

In formulae (IX) and (X), $R_1$ and $R_2$ represent hydrogen atoms, alkyl or aryl groups, or form with the diene grouping a cyclic hydrocarbon containing 5 to 7 carbon atoms, X represents a cyano, carboxy, carbonamido, alkoxycarbonyl or aryloxycarbonyl group. In formula (IX) Z and Z' represent alkyl groups or form with the nitrogen atom a heterocyclic compound possibly having another heteroatom. The transamination reactions are advantageously effected in a solvent, especially an aliphatic chlorinated solvent such as for example methylene chloride or chloroform. The ammonia is advantageously added in the form of an alcoholic solution thereof for example in methanol or ethanol. The temperature may advantageously vary from −30°C. to +25°C.

The azadienes of formula (X) easily cyclise to give pyrazines of the formula (VIII) in the presence of the basic agents. The cyclisation reaction may be carried out for example at the ambient temperature in an aliphatic alcohol with sodium alcoholate as the basic agent. The operation may also be carried out for example under pressure with an alcoholic solution of ammonia at a temperature between 60°C. and 100°C.

On the other hand, the transamination and the cyclisation may be carried out in a single operation without isolation of the aminoazadiene of formula (X). The direct passage to the pyrazine can be effected in an aliphatic chlorinated solvent such as chloroform or methylene chloride by the action of an alcoholic solution of ammonia at a temperature between −30°C. and +25°C. The pyrazine may also be obtained by treatment with an alcoholic solution of ammonia at a temperature between 60°C. and 100°C in an autoclave.

The N-(ZZ')-4-amino-1-cyano-2-aza-1,3-butadienes of formula (IX) may be prepared for example by a general process characterised by reacting an O-tosyl oxime of the general formula:

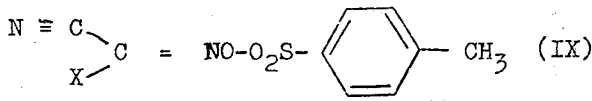

with an aminoalkene or cycloalkene of the general formula:

wherein X, $R_1$, $R_2$, Z and Z' having the same significance as above.

As Examples of compounds of formula (XI) may be mentioned O-tosyl-dicyanoformaldehyde-oxime, O-tosyl-cyano-(methoxy and ethoxy-carbonyl)-formaldehyde-oximes and O-tosyl-cyano-carbonamido-formaldehyde-oxime. These oximes are readily available by conversion of the compounds of formula CN—CH$_2$—X, in which X has the same significance as above, into nitroso compounds and subsequent tosylation (J. M. Biehler et al., Bull.Soc. Chim., 1971, 7, 2711).

As examples of the formula (XII) may be mentioned 1-morpholino-1-butene, -heptene, -cyclopentene- and-cyclohexene, 1-piperidino-1-pentene, and α-pyrrolidino-styrene.

The reaction of the O-tosyl-oximes of formula (XI) with the alkenes or cycloalkenes of formula (XII) is advantageously effected in a solvent. Aliphatic chlorinated solvents such as for example methylene chloride, dichloroethylene, chloroform, and ethers such as for example diethyl oxide or dibutyl oxide are particularly suitable. The operation is preferably carried out in the presence of a compound capable of fixing the p-toluenesulphonic acid liberated in the reaction. For example, a tertiary amine such as triethylamine, pyridine or an excess of aminoalkene of the formula (XII) may be used. The reaction is advantageously carried out at a temperature between −10°C. and +25°C. The azadienes are precipitated, and are generally coloured solids.

In the following examples, which are purely illustrative, the parts indicated are parts by weight unless the contrary is stated.

EXAMPLE 1

A reactor provided with a stirring device, a feed pipe for nitrogen, a bromine feed and a calcium chloride tube is filled with a solution of 15 parts of O-tosyl-C-cyano-C-(ethoxycarbonyl)-formaldehyde-oxime and 5.5 parts of dry triethylamine in 500 parts by volume of dry ether. The solution is cooled to −10°C. and 8.5 parts of 1-morpholino-1-butene diluted in 100 parts by volume of dry ether are slowly added with stirring. The mixture is allowed to react for 6 hours at a temperature of −10°C. and the reaction medium is diluted with 100 parts by volume of ligroin (b.p. 70°–100°C.). The product is left overnight at 0°C. The precipitate obtained is filtered off and washed 3 times on the filter with 100 parts of cold water so as to remove the ammonium salts which accompany the azadiene. The latter is dried and recrystallised from ligroin (b.p. 70°–100°C.). 8 parts of pure 1-cyano-1-ethoxycarbonyl- 3-morpholinomethylene-2-aza-1-pentene (m.p. 127°–128°C.)are thus obtained.

| Analysis | C % | H % | N % |
|---|---|---|---|
| Calculated for $C_{13}H_{19}N_3O_3$: | 58.88 | 7.17 | 15.84 |
| Found: | 59.13 | 7.24 | 15.48 |

EXAMPLE 2

One operates as in Example 1, but the 15 parts of O-tosyl-oxime used are replaced by 12.7 parts of O-tosyl-C-dicyano-formaldehyde-oxime and the 8.5 parts of butene are replaced by 9.2 parts of 1-morpholino-1-cycopentene. 10 parts of 1-dicyanomethyleneamino-2-morpholino-1-cyclopentene are obtained. Melting point 157°–158°C. after recrystallising from absolute alcohol. Yield with respect to the oxime 90%.

| Analysis: | C % | H % | N % |
|---|---|---|---|
| Calculated for $C_{12}H_{14}N_4O$: | 62.6 | 6.09 | 24.35 |
| Found: | 62.5 | 6.18 | 22.86 |

EXAMPLE 3

One operates as in Example 1, but the 8.5 parts of 1-morpholino-1-butene are replaced by 9.2 parts of 1-piperidino-1-pentene. 8.5 parts of 1-cyano-1-ethoxycarbonyl-3-piperidinomethylene-2-aza-1-hexene are thus obtained, which when recrystallised from ligroin melts at 106°C.

| Analysis: | C % | H % | N % |
|---|---|---|---|
| Calculated for $C_{15}H_{23}N_3O_2$: | 64.98 | 8.30 | 15.16 |
| Found: | 64.76 | 8.35 | 15.32 |

EXAMPLE 4

One operates as in Example 1, but the 8.5 parts of 1-morpholino-1-butene are replaced by 11 parts of 1-morpholine-1-heptene. 9 parts of 1-cyano-1-ethoxycarbonyl-3-morpholinomethylene-2-aza-1-octene are obtained which when recrystallised from ligroin, melts at 114°C.

| Analysis: | C % | H % | N % |
|---|---|---|---|
| Calculated for $C_{16}H_{25}N_3O_3$: | 62.54 | 8.14 | 13.68 |
| Found: | 62.63 | 8.27 | 13.87 |

EXAMPLE 5

One operates as in Example 1, but the 8.5 parts of 1-morpholino-1-butene are replaced by 10 parts of α-pyrrolidino-styrene. After reacting for 2 hours at −10°C, 1-cyano-1-ethoxycarbonyl-4-phenyl-4-pyrrolidino-2-aza-1,3-butadiene is obtained with a yield of 95% with respect to the oxime. When recrystallised from alcohol, this product melts at 170°–172°C.

| Analysis: | C % | H % | N % |
|---|---|---|---|
| Calculated for $C_{17}H_{19}N_3O_2$: | 68.7 | 6.40 | 14.14 |
| Found: | 68.9 | 6.41 | 14.03 |

EXAMPLE 6

If in Example 1, the 8.5 parts of 1-morpholino-1-butene are replaced by 9.2 parts of 1-morpholino-1-cyclopentene and the mixture is allowed to react for 4 hours at 25°C. then 1-cyano-1-ethoxycarbonyl-4-morpholino-3,4-trimethylene-2-aza-1,3-butadiene is obtained which, when recrystallised from ethanol, melts at 173°–174°C. Yield: 60% with respect to the oxime.

| Analysis: | C % | H % | N % |
|---|---|---|---|
| Calculated for $C_{14}H_{19}N_3O_3$: | 60.50 | 6.86 | 15.16 |
| Found: | 60.79 | 6.92 | 15.14 |

EXAMPLE 7

If in Example 1 the 8.5 parts of 1-morpholino-1-butene are replaced by 9.5 parts of 1-morpholino-1-cyclohexene and the mixture is allowed to react for 4 hours at 250°C. then 1-cyano-1-ethoxycarbonyl-4-morpholino-3,4-tetramethylene-2-aza-1,3-butadiene is obtained which, when recrystallised from ethanol, melts at 147°–149°C. Yield: 70% with respect to the oxime.

| Analysis: | C % | H % | N % |
|---|---|---|---|
| Calculated for $C_{15}H_{21}N_3O_3$: | 61.85 | 7.22 | 14.43 |
| Found: | 61.05 | 7.44 | 14.35 |

EXAMPLE 8

One operates as in Example 1, but the 15 parts of O-tosyl-C-cyano-C-(ethoxycarbonyl)-formaldehyde-oxime are replaced by 12.7 parts of O-tosyl-C-dicyano-formaldehydeoxime and the 8.5 parts of 1-morpholino-1-butene are replaced by 9.5 parts of 1-morpholino-1-cyclohexene. After reacting for 4 hours at −10°C. one obtains 1-dicyanomethyleneamino-2-morpholino-1-cyclohexane with a yield of 80% with respect to the oxime. When recrystallised from ethanol, the product melts at 143°–145°C.

| Analysis: | C % | H % | N % |
|---|---|---|---|
| Calculated for $C_{13}H_{16}N_4O$: | 63.93 | 6.56 | 22.95 |
| Found: | 63.48 | 6.66 | 22.53 |

EXAMPLE 9

If in Example 1 the 15 parts of O-tosyl-C-cyano-C-(ethoxycarbonyl)formaldehyde-oxime are replaced by 14 parts of O-tosyl-C-cyano-C-(methoxycarbonyl)formaldehyde-oxime and the 8.5 parts of 1-morpholino-1-butene are replaced by 9.5 parts of 1-morpholino-1-cyclohexene and the mixture is allowed to react for 4 hours at 25°C, then 1-cyano-1-methoxycarbonyl-4-morpholino-3,4-tetramethylene-2-aza-1,3-butadiene is obtained which, when recrystallised from methanol, melts at 118°–119°C. Yield: 60% with respect to the oxime.

| Analysis: | C % | H % | N % |
|---|---|---|---|
| Calculated for $C_{14}H_{19}N_3O_3$: | 60.50 | 6.86 | 15.16 |
| Found: | 60.53 | 6.91 | 14.97 |

EXAMPLE 10

If in Example 1 the 8.5 parts of 1-morpholino-1-butene are replaced by 9 parts of 1-piperidino-1-cyclohexene and the mixture is allowed to react for 4 hours at 25°C. then 1-cyano-1-ethoxycarbonyl-4-piperidino-3,4-tetramethylene-2-aza-1,3-butadiene is obtained which, after recrystallisation from ethanol, melts at 100°–101°C. Yield: 65% with respect to the oxime.

| Analysis: | C % | H % | N % |
|---|---|---|---|
| Calculated for $C_{16}H_{23}N_3O_2$: | 66.43 | 7.95 | 14.53 |
| Found: | 65.88 | 7.84 | 14.8 |

EXAMPLE 11

One operates as in Example 1, but the 15 parts of O-tosyl-C-cyano-C-(ethoxycarbonyl)formaldehydeoxime are replaced by 12.7 parts of O-tosyl-C-dicyanoformaldehydeoxime and the 8.5 parts of 1-morpholino-1-butene are replaced by 9 parts of 1-piperidino-1-cyclohexene. After reacting for 4 hours at −10°C. one obtains 1-dicyano-methyleneamino-2-piperidino-1-cyclohexene in a yield of 89% with respect to the oxime. After recrystallisation from ethanol, this product melts at 127°–129°C.

| Analysis: | C % | H % | N % |
|---|---|---|---|
| Calculated for $C_{14}H_{18}N_4$: | 69.42 | 7.44 | 23.14 |
| Found: | 69.74 | 7.85 | 22.9 |

EXAMPLE 12

Preparation of 1-cyano-1-ethoxycarbonyl-4-phenyl-2-aza-1,3-butadiene

A reactor provided with a stirring device, a bromine feed and a calcium chloride tube, is filled with a solution of 6.3 parts of 1-cyano-1-ethoxycarbonyl-4-morpholino-4-phenyl-2-aza-1,3-butadiene in 63 parts by volume of dry methylene chloride. 1.4 parts by weight of ammonia (in the form of a concentrated solution in ethanol) are added at the ambient temperature over a period of three days.

The reaction is allowed to finish over a further day and the solvents are removed under reduced pressure. 8.8 parts of 1-cyano-1-ethoxycarbonyl-4-amino-4-phenyl-2-aza-1,3-butadiene are thus obtained. After recrystallising from absolute alcohol, this melts at 139°–140°C.

| Analysis: | C % | H % | N % |
|---|---|---|---|
| Calculated for $C_{13}H_{13}N_3O_2$: | 64.19 | 5.34 | 17.28 |
| Found: | 64.13 | 5.35 | 17.26 |

EXAMPLE 13

Preparation of 1-cyano-1-methoxycarbonyl-3-methyl-4-amino-4-phenyl-2-aza-1,3-butadiene One operates as in Example 12, but the 1-cyano-1-ethoxycarbonyl-4-morpholino-4-phenyl-2-aza-1,3-butadiene is replaced by 1-cyano-1-methoxycarbonyl-3-methyl-4-morpholino-4-phenyl-2-aza-1,3-butadiene and the reaction is effected at −30°C. 4.1 parts of 1-cyano-1-methoxycarbonyl-3-methyl-4-amino--4-phenyl-2-aza-1,3-butadiene are obtained after a reaction time of 3 days. After recrystallisation from methanol the product melts at 145°C.

| Analysis: | C % | H % | N % |
|---|---|---|---|
| Calculated for $C_{13}H_{13}N_3O_2$: | 64.19 | 5.34 | 17.28 |
| Found: | 64.13 | 5.49 | 17.31 |

EXAMPLE 14

Preparation of 1-cyano-1-methoxycarbonyl-4-amino-4-phenyl-2-aza-1,3-butadiene

One operates as in Example 12, but the 6.3 parts of 1-cyano-1-ethoxycarbonyl-4-morpholino-4-phenyl-2-aza-1,3-butadiene are replaced by 6 parts of 1-cyano-1-methoxy-carbonyl-4-morpholino-4-phenyl-2-aza-1,3-butadiene. 3.7 parts of 1-cyano-1-methoxycarbonyl-4-amino-4-phenyl-2-aza-1,3-butadiene are obtained. After recrystallisation from methanol, the product melts at 186°C.

| Analysis: | C % | H % | N % |
|---|---|---|---|
| Calculated for $C_{12}H_{11}N_3O_2$: | 62.88 | 4.81 | 18.34 |
| Found: | 62–84 | 4.96 | 18.38 |

EXAMPLE 15

Preparation of 2-methoxycarbonyl-3-amino-5-phenyl-6-methyl-pyrazine

A reactor provided with a stirring device, a bromine feed and a calcium chloride tube is filled with a solution of 4 parts of 1-cyano-1-methoxycarbonyl-3-methyl-4-amino-4-phenyl-2-aza-1,3-butadiene in 120 parts by volume of a mixture of dry methanol and dry methylene chloride (10 : 1 by volume.) 0.9 parts of sodium methylate dissolved in dry methanol are added rapidly at the ambient temperature with stirring. The reaction is finished at the end of 15 minutes, and the greater part of the solvents is evaporated under reduced pressure. The 2-methoxycarbonyl-3-amino-5-phenyl-6-methyl pyrazine which is precipitated is filtered off, then recrystallised from methanol and 3 parts of pyrazine are obtained. M.p. 162°C.

EXAMPLE 16

Direct preparation of 2-methoxycarbonyl-3-amino-5-phenyl-6-methyl-pyrazine in an autoclave An autoclave fitted with a stirring device and surrounded by a heating jacket is filled with 3.1 parts of 1-cyano-1-methoxycarbonyl-3-methyl-4-morpholino-4-phenyl-2-aza-1,3-butadiene in 110 parts by volume of a mixture of dry methanol and dry methylene chloride (10 : 1) and 0.255 parts by weight of annomia in the form of a concentrated methanolic solution. After reacting for 4 hours at 85°C. one obtains 1.5 parts of 2-methoxy-carbonyl-3-amino-5-phenyl-6-methyl-pyrazine. After recrystallisation from methanol, the melting point is 162°–163°C.

| Analysis: | C % | H % | N % |
|---|---|---|---|
| Calculated for $C_{13}H_{13}N_3O_2$: | 64.19 | 5.34 | 17.28 |
| Found: | 63.40 | 5.54 | 17.24 |

EXAMPLE 17

Preparation of 2-methoxycarbonyl-3-amino-5-phenyl-pyrazine

One operates as in Example 15, but the 4 parts of 1-cyano-1-methoxycarbonyl-3-methyl-4-amino-4-phenyl-2-aza-1,3-butadiene are replaced by 3.8 parts of 1-cyano-1-methoxy-carbonyl-4-amino-4-phenyl-2-aza-1,3-butadiene. 3.66 parts of 2-methoxycarbonyl-3-amino-5-phenyl-pyrazine are obtained. After recrystallisation of the product from methanol the melting point is 228°C.

| Analysis: | C % | H % | N % |
|---|---|---|---|
| Calculated for $C_{12}H_{11}N_3O_2$: | 62.88 | 4.81 | 18.34 |
| Found: | 62.74 | 4.69 | 18.43 |

EXAMPLE 18

Preparation of 2-cyano-3-amino-5-phenyl-6-methyl-pyrazine

A reactor provided with a stirring device, a bromine feed and a calcium chloride tube is filled with 1.42 parts of 1,1-dicyano-3-methyl-4-morpholino-4-phenyl-2-aza-1,3-butadiene in 20 parts by volume of dry methylene chloride. 0.34 parts by weight of ammonia in the form of a methanolic solution are added at −30°C. over a period of 4 days. After evaporation of the solvents in vacuo and recrystallisation of the crude product from methanol, 0.95 parts of 2-cyano-3-amino-5-phenyl-6-methyl-pyrazine are obtained in a field of 91% with respect to the starting azadiene.

| Analysis: | C % | H % | N % |
|---|---|---|---|
| Calculated for $C_{12}H_{10}N_4$: | 68.60 | 4.77 | 26.63 |
| Found: | 68.61 | 4.70 | 26.69 |

EXAMPLE 19

Preparation of 2-cyano-3-amino-5,6-tetramethylenepyrazine

One operates as in Example 18, but the 1.4 parts of 1,1-dicyano-3-methyl-4-morpholino-4-phenyl-2-aza-1,3-butadiene are replaced by 1.2 parts of 1,1-dicyano-3,4-tetramethylene-4-morpholino-2-aza-1,3-butadiene, the reaction being carried out at 20°C. After recrystallisation from methanol, 0.83 parts of 2-cyano-3-amino-5,6-tetramethylenepyrazine are obtained.

| Analysis: | C % | H % | N % |
|---|---|---|---|
| Calculated for $C_9H_{10}N_4$: | 62.10 | 5.75 | 32.15 |
| Found: | 61.99 | 5.86 | 31.98 |

We claim:

1. A process for the preparation of an aminopyrazine represented by the formula:

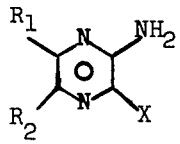

in which $R_1$ and $R_2$ each represent hydrogen, alkyl having from 1 to 5 carbon atoms, or phenyl, or together with the carbon atoms of the pyrazine ring to which they are linked form a cycloalkene having from 5 to 7 carbon atoms in the ring, and X represents cyano, carboxy, carbonamide or alkoxycarbonyl having from 1 to 4 carbon atoms in the alkoxy chain which consists in contacting a 1-cyano-4-N(disubstituted) amino-2-azo-1,3-butadiene of the formula:

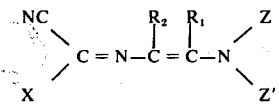

wherein Z and Z' together with the nitrogen atom form a morpholino, piperidino or pyrrolidino group, which may be unsubstituted or substituted by one or several lower alkyl groups, with ammonia in the presence of a solvent and reacting the 1-cyano-4-amino-2-aza-1,3-butadiene of the formula:

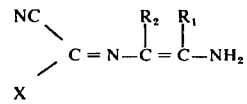

thus obtained with a basic agent selected from the group consisting of alcoholoates, ammonia, amines and quaternary ammonium hydroxides.

2. Process according to claim 1 wherein the basic agent is sodium alcoholate and the reaction with the basic agent is effected in an aliphatic alcohol at ambient temperature.

3. Process according to claim 1 wherein the basic agent is an alcoholic solution of ammonia and the reaction with the basic agent is effected under pressure at a temperature of from 60°C to 100°C.

4. Process according to claim 1 wherein ammonia is the basic agent and the contact between ammonia and the 1-cyano-4-N(disubstituted) amino-2-aza-1,3-butadiene is effected in the presence of a solvent selected from the group consisting of halogenated aliphatic hydrocarbons and halogenated aromatic hydrocarbons.

5. Process according to claim 4 wherein the solvent is a chlorinated aliphatic hydrocarbon having 1 or 2 carbon atoms.

6. Process according to claim 1 wherein ammonia is the basic agent and is used in alcoholic solution for contact with the 1-cyano-4-N(disubstituted) amino-2-aza-1,3-butadiene.

7. Process according to claim 1 wherein ammonia is the basic agent and the contact between ammonia and the 1-cyano-4-N(disubstituted) amino-2-aza-1,3-butadiene is effected at a temperature of from −30°C to 25°C.

8. Process according to claim 1 wherein there is no isolation of the 1-cyano-4-amino-2-aza-1,3-butadiene.

9. Process according to claim 8 wherein the 1-cyano-4-N(disubstituted) amino-2-aza-1,3-butadiene is reacted with an alcoholic solution of ammonia.

10. Process according to claim 9 wherein the reaction is effected in an autoclave at a temperature of from 60°C to 100°C.

11. Process according to claim 9 wherein the reaction is effected at a temperature of from −30°C to +25°C in the presence of a solvent selected from the group consisting of halogenated aliphatic hydrocarbons and halogenated aromatic hydrocarbons.

12. Process according to claim 1 wherein the 1-cyano-4-N-(disubstituted) amino-2-aza-1,3-butadiene is prepared by reacting an O-tosyl oxime of the formula:

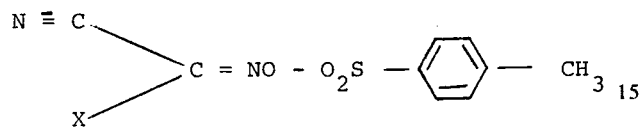

with an aminoalkene or cycloalkene of the formula:

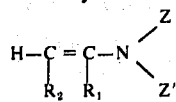

wherein X, $R_1$, $R_2$, Z and Z' have the meanings given in claim 1.

13. Process according to claim 12 wherein the reaction is effected in a solvent selected from the group consisting of chlorinated aliphatic hydrocarbons and ethers.

14. Process according to claim 12 wherein the reaction is effected in the presence of a tertiary amine or an excess of the aminoalkene or cycloalkene.

15. Process according to claim 12 wherein the reaction is effected at a temperature of from −10°C to +25°C.

* * * * *

UNITED STATES PATENT OFFICE
CERTIFICATE OF CORRECTION

PATENT NO. : 3,932,404
DATED : January 16, 1976
INVENTOR(S) : JEAN-PIERRE LOUIS FLEURY It is certified that error appears in the above-identified patent and that said Letters Patent are hereby corrected as shown below:

In the heading on page 1 column 1, line 30 delete "Foreign

Application Priority Data

January 20, 1972 France . . . . 7201854 . . ."

*Signed and Sealed this*

*twenty-fifth* Day of *May 1976*

[SEAL]

Attest:

RUTH C. MASON
*Attesting Officer*

C. MARSHALL DANN
*Commissioner of Patents and Trademarks*